United States Patent
Zhou et al.

(10) Patent No.: US 7,672,733 B2
(45) Date of Patent: Mar. 2, 2010

(54) METHODS AND APPARATUS FOR SENSING CARDIAC ACTIVITY VIA NEUROLOGICAL STIMULATION THERAPY SYSTEM OR MEDICAL ELECTRICAL LEAD

(75) Inventors: Xiaohong Zhou, Plymouth, MN (US); Thomas J. Mullen, Andover, MN (US); Michael R. S. Hill, Minneapolis, MN (US); Steve R. Laporte, Rhinelander, WI (US); Gary W. King, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 476 days.

(21) Appl. No.: 11/116,970

(22) Filed: Apr. 28, 2005

(65) Prior Publication Data

US 2006/0095081 A1     May 4, 2006

Related U.S. Application Data

(60) Provisional application No. 60/623,493, filed on Oct. 29, 2004.

(51) Int. Cl.
*A61N 1/05* (2006.01)
*A61N 1/08* (2006.01)
*A61N 1/365* (2006.01)

(52) U.S. Cl. .......................... 607/117; 607/11
(58) Field of Classification Search ............... 607/117, 607/118, 9, 11, 17
See application file for complete search history.

(56) References Cited

U.S. PATENT DOCUMENTS

| 5,058,584 | A | 10/1991 | Bourgeois | |
| 5,199,428 | A | 4/1993 | Obel et al. | |
| 5,324,323 | A | 6/1994 | Bui | |
| 5,330,507 | A * | 7/1994 | Schwartz | 607/14 |
| 5,578,061 | A * | 11/1996 | Stroetmann et al. | 607/4 |
| 5,824,021 | A | 10/1998 | Rise | |
| 5,916,239 | A * | 6/1999 | Geddes et al. | 607/14 |
| 5,928,272 | A | 7/1999 | Adkins et al. | |
| 6,134,470 | A | 10/2000 | Hartlaub | |
| 6,885,888 | B2 * | 4/2005 | Rezai | 607/9 |
| 7,162,304 | B1 * | 1/2007 | Bradley | 607/46 |
| 2002/0107553 | A1 | 8/2002 | Hill | |
| 2002/0143369 | A1 | 10/2002 | Hill | |
| 2002/0165586 | A1 | 11/2002 | Hill | |
| 2003/0004549 | A1 * | 1/2003 | Hill et al. | 607/9 |
| 2003/0040774 | A1 | 2/2003 | Terry et al. | |
| 2003/0045909 | A1 * | 3/2003 | Gross et al. | 607/9 |
| 2003/0060858 | A1 * | 3/2003 | Kieval et al. | 607/44 |
| 2004/0162590 | A1 | 8/2004 | Whitehurst et al. | |
| 2004/0193021 | A1 | 9/2004 | Zdeblick et al. | |
| 2004/0210261 | A1 * | 10/2004 | King et al. | 607/9 |

OTHER PUBLICATIONS

PCT Search Report, PCT/US2005/039359, 3 pages.

* cited by examiner

*Primary Examiner*—Carl H. Layno
*Assistant Examiner*—Tammie K. Heller
(74) *Attorney, Agent, or Firm*—Stephen W. Bauer (57) ABSTRACT

According to the present invention at least a pair of neurological stimulation electrodes are disposed in, on, about, adjacent and/or within excitable neural tissue of a subject. Cardiac activity of a patient is detected using one or more electrodes adapted for delivery of a neurological stimulation therapy (NST). Following detection of certain types of cardiac activity one or more of the plurality of stimulation electrodes deliver or withhold NST, if desired in synchrony with the cardiac activity or in response to the detected cardiac activity. The NST delivered includes without limitation subcutaneous stimulation, peripheral, TENS and/or vagal nerve stimulation therapy or the like.

3 Claims, 9 Drawing Sheets

METHODS AND APPARATUS FOR SENSING CARDIAC ACTIVITY VIA NEUROLOGICAL STIMULATION THERAPY SYSTEM OR MEDICAL ELECTRICAL LEAD

STATEMENT OF PRIORITY AND INCORPORATION BY REFERENCE

This non-provisional U.S. patent application hereby claims the benefit of prior U.S. provisional patent application Ser. No. 60/623,493 which was filed 29 Oct. 2004 and is entitled, "METHOD AND APPARATUS FOR DETECTING CARDIAC ACTIVITY VIA AT LEAST ONE ELECTRODE DISPOSED IN OR ADJACENT TO THE SPINAL COLUMN" the contents of which are incorporated by reference herein as if fully set forth in the body of the instant document.

FIELD OF THE INVENTION

This invention relates to apparatus and methods for sensing cardiac activity electrical signals and for optionally providing electrical neurological stimulation therapy at one or more neural sites using one or more neurological stimulation electrodes operatively coupled to excitable neural tissue of a subject (e.g., in or adjacent to the spinal column and spaced from the myocardium).

BACKGROUND OF THE INVENTION

Various extant electrical therapies for a variety of cardiac and neurological disorders operate by delivering electrical stimulation to a portion of myocardium, a spinal cord, a part of the vagus nerve bundle, and/or other nerve fibers that affect a bodily function and/or an organ of the body, etc. Typically, nerve stimulation therapy was manually initiated or triggered by a patient when the patient becomes symptomatic. Depending on the location of neurological stimulation therapy delivery, remote monitoring of an affected organ can increase the complexity of an implantable therapeutic apparatus and/or the risk to a patient from various complications.

A need exists in the art for so-called closed loop neurological therapy delivery, including therapeutic neurological stimulation based at least in part on the monitoring of an affected organ that is located remotely from the site or sites of neurological therapy.

SUMMARY OF THE INVENTION

Systems and methods according to the invention provide for remote monitoring of the condition or functioning of a subject's organ (e.g., cardiac activity signals from a location spaced from the heart) using one or more electrodes adapted to deliver neurological therapy positioned in electrical communication with excitable neural tissue of a subject (e.g., in, on, or near excitable neural tissue).

The electrodes may comprise one or more skin-based electrodes as well as subcutaneous and/or submuscular electrodes that are operatively electrically coupled to excitable spinal cord tissue from a location on, in or near the spinal cord, or near other excitable neural tissue. The system further includes a controller coupled to the electrodes for processing the physiologic signal from the monitored organ and delivering neurological therapy on demand or as dictated by a neurological therapy delivery algorithm. The controller may be external to an internal site or sites of neurological therapy delivery, subcutaneously placed, or fully implanted within a patient's body. The system may additionally include a variety of optional electrodes and medical devices (e.g., drug delivery pumps) but in an exemplary embodiment is devoid of transvenous and/or endocardial sensors and other components. The optional electrodes or devices may be partly or wholly externally located, subcutaneously placed, or fully implanted. Any component of the system may be electrically connected to any other component through conductive leads or wires, or in wireless communication with any other component. The system is adapted to remotely monitor physiologic conditions of an organ using sensing vectors defined by a pair of the neurological therapy delivery electrodes or by a single electrode electrically coupled to a conductive portion of a housing for the controller. Neurological stimulation therapy or other therapy is initiated and modulated based on the time-varying physiological condition of said organ, due at least in part to the fact that the organ is directly or indirectly affected by the neurological stimulation.

The present invention also includes computer readable media for storing instructions that cause a processor-controlled apparatus to execute the methods of the invention. The media includes all media now known or later developed including magnetically-encoded media, optically-encoded media, FLASH and programmable logic circuits and arrays and the like including equivalents thereof.

A current spinal cord stimulation (SCS) device used for angina pectoris uses an open-loop mode for stimulation. In contrast, in one embodiment the present invention includes a modified SCS device operating as a closed-loop device so that the therapy can be timely applied once myocardial ischemia or other cardiac dysfunction is detected remotely using the SCS electrodes. Thus, the invention helps improve the efficacy of a neurological stimulator and at the same time increase service life or longevity of the device due to only delivering neurological stimulation at certain times and/or in response to detected cardiac condition (e.g., ischemia, heart rate variability, high or low heart rate, etc.) and/or withholding neurological stimulation in response to cardiac activity or condition. In another embodiment of the invention, neurological stimulation therapy electrodes adapted to couple to the vagus nerve are employed to remotely monitor cardiac conditions. Herein such neurological stimulation shall be referred to from time to time as Neurological Stimulation Therapy (NST) which shall comprehend all forms of electrical therapy directed to a portion of the nervous system of a subject.

A specific advantage is to improve ischemia detection, especially to improve detection of posterior myocardial ischemia and infarction. In addition, the cardiac signal recorded by a neurological lead and device can be used for detection of cardiac arrhythmias and monitoring of Q-T intervals, T-wave changes (e.g., alternans) as well as autonomic indicators such as heart rate variability and heart rate turbulence. Importantly, the invention does not require an intracardiac lead for monitoring cardiac activity. Therefore, a closed-loop neural stimulation can be achieved with the information from cardiac electrical signals. By example and without limitation the following features of the invention summarize certain aspects of the invention: (1) neurological stimulation-type medical electrical leads with capability for cardiac sensing; (2) neural stimulation device with capability of cardiac sensing; (3) algorithm for filtering artifacts due to neurological stimulation device and/or myopotentials due to patient activity; and (4) delivery of neurostimulation synchronized with cardiac electrical or mechanical cycles.

In still another aspect of the instant invention, methods are provided. Certain methods comprise providing at least one NST electrode in a region associated with excitable nervous tissue of a patient and applying electrical stimulation via the at least one NST electrode to alter the functioning of a patient's heart. One or more predetermined physiologic cardiac parameters of the patient are remotely monitored via the NST electrodes, and the electrical stimulation is adjusted based on the one or more predetermined physiologic parameters.

In another embodiment, an apparatus is provided comprising at least one electrode that may be positioned in a region associated with central nervous tissue of a patient. Structural means for controlling the delivery of NST delivery to alter functioning of a patient's heart is also provided. The controlling means utilizes one or more predetermined cardiac parameters of the patient, and the electrical stimulation is adjusted based on the one or more predetermined parameters.

BRIEF DESCRIPTION OF THE DRAWINGS

The present invention is described and depicted herein using a limited set of drawings wherein like components are referred to by like reference numerals and the drawings are not drawn to scale nor intended to illustrate any unrelated components or ancillary method steps. Those of skill in the art to which the invention is directed will appreciate insubstantial modifications or changes to the invention each of which is intended to be expressly covered hereby.

DETAILED DESCRIPTION OF ILLUSTRATED EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Illustrative embodiments of a method and apparatus for providing improved cardiac function according to the present invention are shown in the Figures. As will be readily apparent to those skilled in the art upon a complete reading of the present application, the present method and apparatus are applicable to a variety of systems other than the embodiment illustrated herein.

Figure 1A:
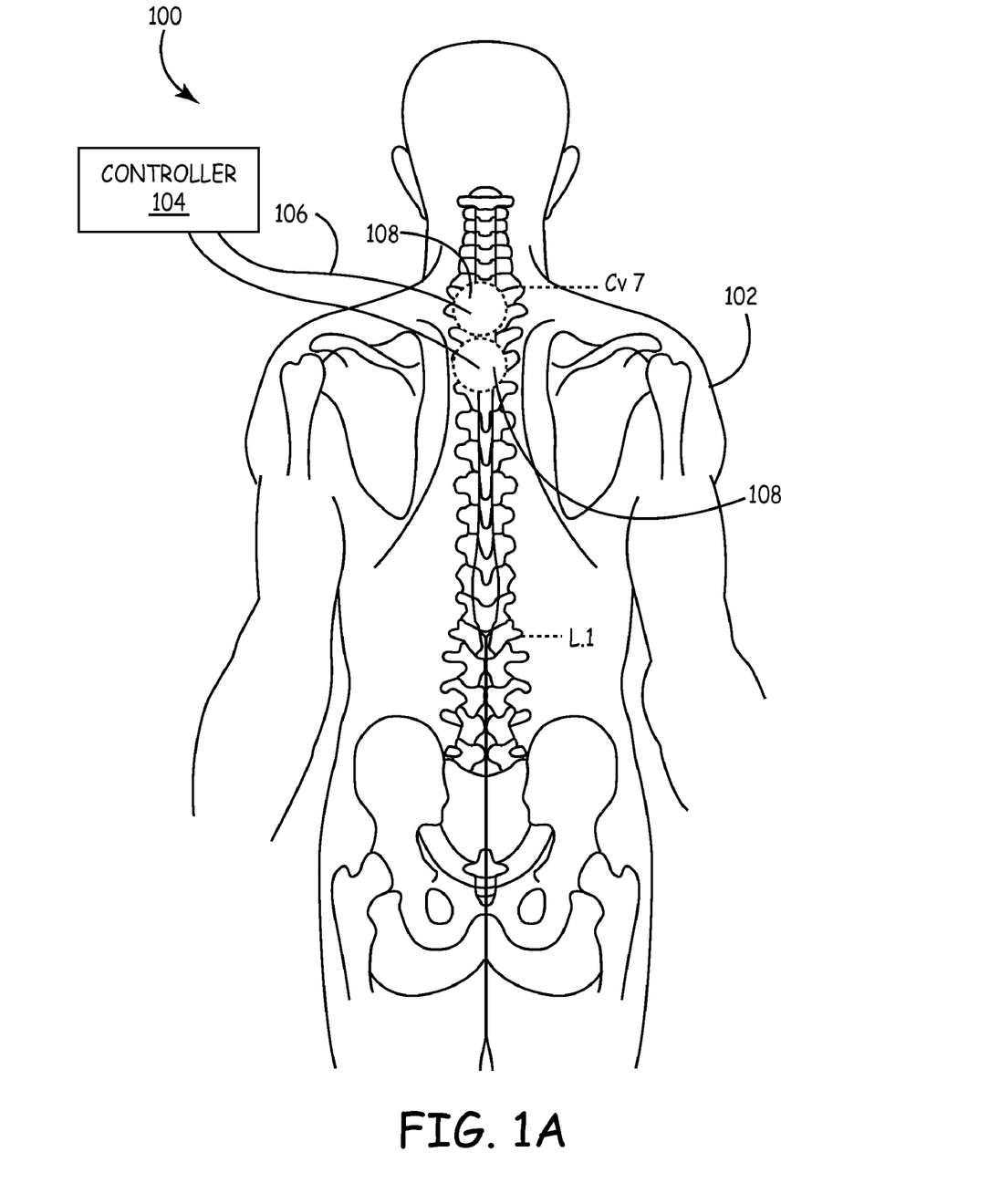
FIG. 1A illustrates a stylized representation of a posterior view of a patient with electrodes positioned thereon.
Figure 1B:
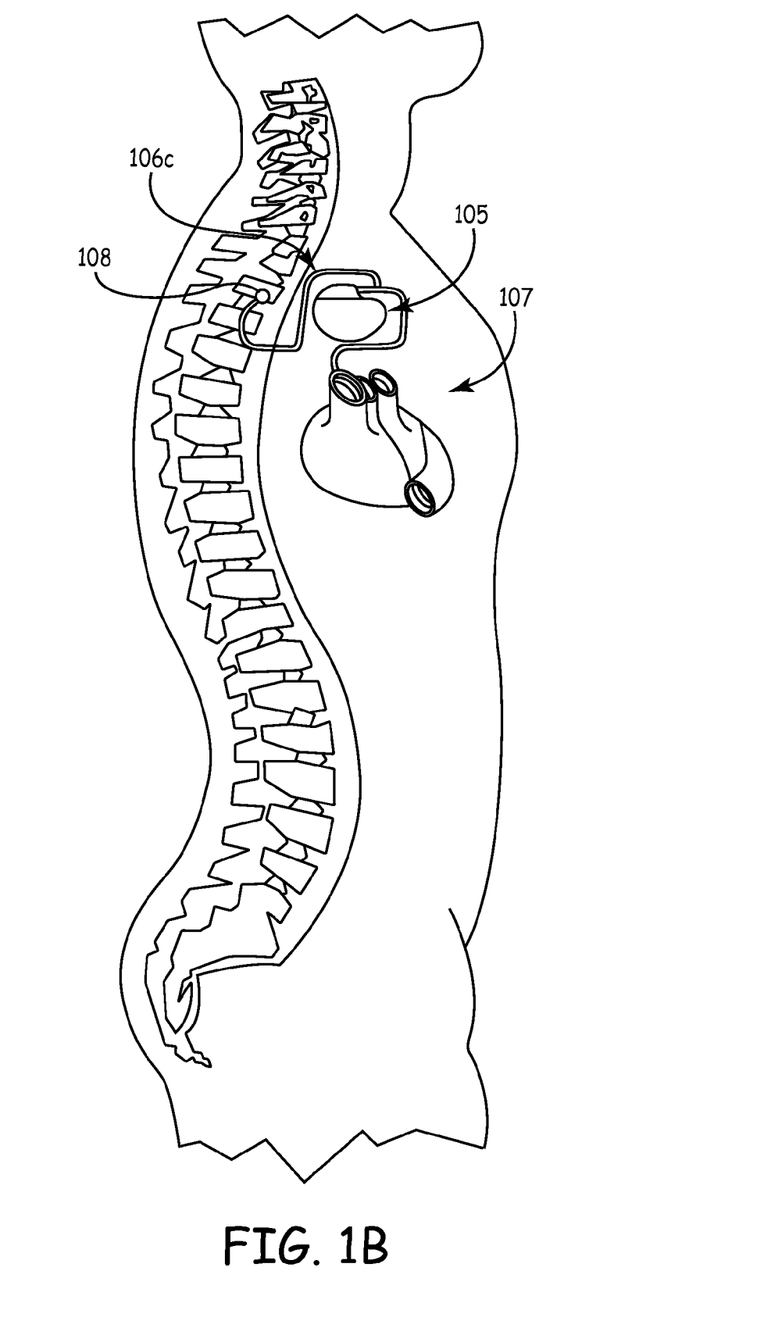
FIG. 1B is a diagram illustrating an implantable stimulation device implanted within a patient.

Generally, the instant invention is directed to a method and apparatus for improving cardiac performance (e.g., hemodynamics) and efficiency (e.g., balance between supply and demand and balance within the neuro-endocrinological systems) of the patient's heart. In the illustrated embodiment, the current invention utilizes electrical stimulation to treat ventricular dysfunction or heart failure. As shown in FIGS. 1A and 1B, a system 100 may provide Neural Stimulation Therapy (NST) (e.g. SCS, TENs, sub-cutaneous stimulation, peripheral nerve stimulation) to a patient 102 adjacent one or more of the locations T1-T12, and C1-C8 or to nerves on the chest, to improve cardiac performance and efficiency. Such stimulation has been shown to stabilize cardiac electrical activity, to reduce sympathetic activity of the cardiac tissue, to improve the cardiac condition, and to reduce the likelihood of ventricular arrhythmias. Thus, the electrical stimulation produces effects similar to those induced by prescription beta-adrenergic receptor blocking drugs. SCS has been shown to vasodilate peripheral arterioles and increase blood flow to the limbs. SCS may further cause the production of neuropeptides such as CGRP, NO, and VIP that are known vasodilators, which may assist in redirection of blood flow from regions of high flow to regions of low flow. This further improves the performance and efficiency of the heart. In the ischemic dilated cardiomyopathy patients, this therapy may suppress or reduce sub-endocardial ischemia, and hence be cardio-protective. Electrical stimulation may further result in improvements in operational efficiency and function of cardiac tissue even in the presence of reduced blood supply.

A controller 104 is coupled through conventional conductive links 106, such as leads or wires, to one or more electrodes 108 mounted in a region adjacent the T1-T12 and C1-C8 vertebrae and their associated nerve bundles. The electrodes 108 may take on any of a variety of forms, including but not limited to conventional surface mounted 1 electrodes, such as are commonly used in conjunction with Transcutaneous Electrical Neurological Stimulator (TENS) units. These surface mounted electrodes may be fixed to the patient 102 via any of a variety of conventional mechanical or chemical mechanisms or may be simply held in place by friction and gravity. Alternatively, conventional implantable electrodes may be surgically inserted into the spinal region adjacent the T1-T12 and C1-C8 vertebrae, and may be located near or even immediately adjacent the T1-T12 and C1-C8 nerve bundles for spinal cord stimulation.

Implantable electrodes may be placed subcutaneously to stimulate underlying muscles, overlying cutaneous nerves, or passing somatic nerves. For example, lead Model 3987, is a peripheral nerve stimulation lead available from Medtronic, Inc. with four contacts and a polyester mesh skirt for fixation to subcutaneous tissue or muscle fascia. Other Medtronic leads might also be used, including Model 3587A or Model 3998, which have an insulative paddle enlargement, or Model 3487A or Model 3888, which do not. In both surface mounted and implanted electrodes, electrical signals supplied by the controller 104 to the electrodes 108 electrically stimulate nervous tissue in the spinal canal, sometimes by activating axons in nerves that connect to the spinal cord Implantable electrodes may be placed adjacent to nerves such as the median, peroneal, ulnar, and ansa lenticularis nerves to provide stimulation according to the current invention. Similarly, implantable electrodes may be placed near the vagus nerves, carotid sinus, and all other cranial nerves to provide stimulation. Finally, implantable electrodes may be placed epicardially or transvenously near the cardiac ganglia or plexi and also employed in this manner.

The controller 104 may take the form of an external device or an implantable device. Where the controller 104 is an external device, it may be useful in providing therapeutic signals to a patient who is experiencing an unexpected cardiac event, such as a first or otherwise unanticipated episode of ventricular dysfunction, heart failure, cardiovascular collapse, etc. However, where the patient has a history of cardiac events, it may prove useful to construct the controller 104 in a housing designed to be implantable within the human body, such as is common in cardiac pacemakers and defibrillators. The controller 104 may be programmed for either automatic or manual operation. That is, the controller 104 may have one or more conventional sensors (not shown) of a type capable of sensing a cardiac event or a precursor to a cardiac event in the patient (e.g., a decompensation episode of ventricular dysfunction, heart failure, and cardiovascular collapse). The sensors and control scheme used to detect the cardiac event or a precursor to a cardiac event may be conventional, such as is found in implantable defibrillators or pacemakers. Upon detection of the cardiac event, the controller 104 may automatically begin therapeutic treatment of the patient by electrically stimulating the T1-T12 spinal nerves or parts of the cervical or thoracic spinal cord. Alternatively, a patient or authorized person may manually activate the controller 104 to begin this therapeutic treatment. Manual activation may be accomplished by any of a variety of mechanisms. For example, where the controller 104 is implanted in the patient, activation may be accomplished by wireless communication or the like.

In those situations in which a patient has a history of cardiac events, it is generally useful to construct the controller 104 in a housing 105 designed to be implantable within the human body, as shown in FIG. 1B. In this embodiment, implanted lead 106 [change 106c to 106 in the drawing] is employed to deliver SCS according to the invention.

The therapeutic treatment administered by the controller 104 may take on a variety of different forms. In one embodiment, NST (e.g., SCS) delivery can be used to titrate the pressure-volume relationship of the heart in conjunction with other types of therapy, such as one or more types of pacing therapies. For example, an adjustment of the atrio-ventricular (AV) and ventricular-ventricular (V-V) timing during atrial-synchronized bi-ventricular pacing (which is one form is known as cardiac resynchronization therapy or CRT) can be performed at about the same time as the NST delivery to further improve the performance and efficiency of the heart.

Additionally, the stimulation therapy may be administered along with cardiac resynchronization therapy to further improve the cardiac performance and efficiency of the heart. That is, the SCS or another NST (e.g. TENs, subcutaneous) therapy may be administer shortly before, shortly after, or at the same time as resynchronization or other pacing therapy. For example, the SCS therapy can be administered in conjunction with bradycardia pacing therapy, such as those causing changes in the lower rate limit (LRL—atrial or ventricle); therapies for increasing cardiac output or pulse pressure, such as post extra-systolic potentiation (PESP) pacing or non-excitatory stimulation (NES) pacing; and/or therapies for preventing arrhythmias or reducing arrhythmic burden, such including arrhythmia prevention pacing algorithms, such as consistent A or V pacing and rate stabilization pacing. In particular, one exemplary scheme involves administering the stimulation therapy in conjunction with overdrive RV apical pacing to provide improved cardiac output for example in patients with obstructive cardiomyopathies. In addition, the therapy may be administered in conjunction with other device therapies to further improve the cardiac performance and efficiency of the heart. These device therapies may include, but are not limited to, drug delivery device therapies, automatic external defibrillation therapies, treatments provided by monitoring or diagnostic devices, and therapies provided in conjunction with patient management and information tools.

In one embodiment, delivery of the SCS therapy may be modified based on a variety of measurable physiologic parameters. As depicted in FIGS. 1A and 1B, representative sensors (not depicted) may be positioned adjacent or within the body of the patient 102 to sense various physiological conditions, which are communicated back to the controller 104 over a conductive lead or leads. The measured physiological conditions may be used as an indication of the patient's response to the therapy being administered by the controller 104. For example, a positive physiological response may be used as an indication that the therapy is achieving the desired result. The sensed physiological conditions may be used to adjust the parameters of the SCS. For example, the controller 104 may measure and record cardiac pressure. A change in the cardiac pulse pressure may be used in a closed-loop system to adjust delivery of SCS. For example, if the controller 104 detects that the cardiac pulse pressure has declined over time, then the parameters of the SCS may be adjusted in an attempt to increase the cardiac pulse pressure. On the other hand, where the controller 104 observes a consistent, appropriate cardiac pulse pressure, then the stimulation delivered to the T1-T12 nerve bundles may be continued, as a desired result is being achieved by the SCS. On the other hand, where the controller 104 observes continued high, or even rising, cardiac pulse pressure, then the parameters of the NST may be adjusted in an attempt to lower the cardiac pulse pressure over time.

Other parameters that may be measured and used as feedback in a closed loop control system for NST delivery include, but are not limited to, pressure-volume (PV) loops, pressure-area (PA) loops, pressure-dimension (PD) loops, diastolic and systolic pressures, estimated pulmonary artery pressure, change in cardiac pulse pressure, pre-ejection timing intervals, heart rate measures (such as, rates, intervals, and the like), autonomic indicators (such as, heart rate variability, direct neural recordings, and the like), chemical sensors (such as, catecholamines, $O_2$ (saturated venous and/or arterial), pH, CO2, and the like), or non-cardiac physiologic sensors (such as, activity, respiratory rate, time of day, posture, and the like). Those skilled in the art will appreciate that any of a wide variety of measurable physiologic parameters may be monitored and used to implement the closed-loop adaptive controller described herein. An exemplary controller is described in greater detail in co-pending U.S. patent application Ser. No. 10/035,319 entitled "Closed-Loop Neuromodulation for Prevention and Treatment of Cardiac Conditions" filed on 26 Oct. 2001, and the contents of which are entirely incorporated herein by reference.

Any combination of the foregoing may be used to determine the timing, waveforms, and amplitude of the electrical stimulation delivered to the electrodes 108. Those skilled in the art will appreciate that the illustrated, representative sensor may take on any of a variety of forms, depending upon the physiological parameter being sensed. Generally, these feedback parameters may be detected and used to control certain parameters of the stimulation, such as the magnitude, duration, duty cycle, and frequency. Typically, the stimulation falls within the range of about 200-400 microsecond duration pulses, at a frequency in the range of about 50-100 Hz, and at a voltage of up to about 6V. For example, with greater stimulation parameters (increased magnitude, increased frequency, increased duty cycle, and/or increased pulse durations, there is a potential for greater beta-blocker type (withdrawal of sympathetic activity) effect. This would result in decreased contractility, alteration in blood flow (increase in coronary supply), improved cardioprotection and decreased workload or demand. An additional example is the appropriate use of pre-set parameters in response to sensed cardiac event information of the patient. For example, if the patient is having a decompensation ventricular dysfunction or heart failure event, then "more strenuous" stimulation parameters (e.g. increased magnitude, increased pulse width and increased frequency) may be used to provide the greatest amount of protection and local withdrawal of sympathetic activity. For a less severe event, such as an elevation in end diastolic pressure, then "less strenuous" stimulation parameters may be used to provide an incremental adjustment to the cardiac function.

Figure 2:
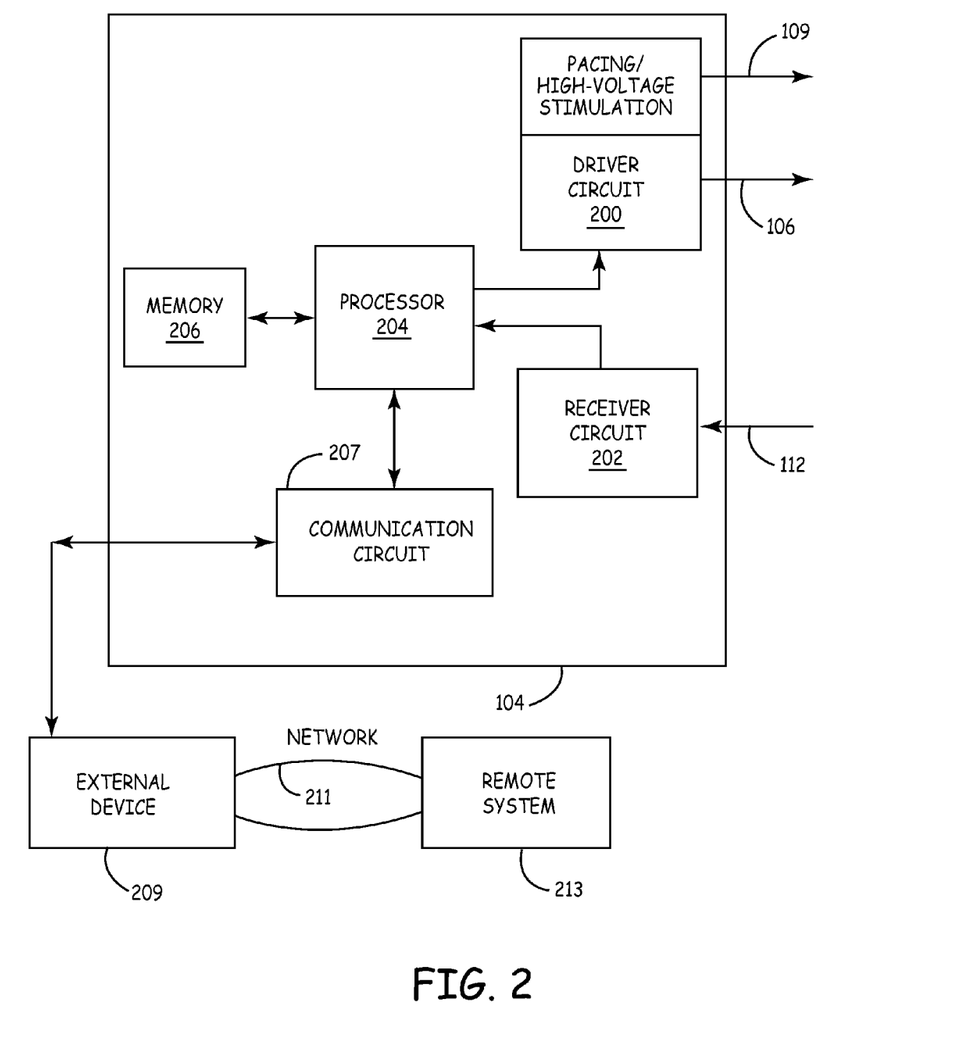
FIG. 2 illustrates a stylized block diagram of a controller of FIG. 1.

FIG. 2 illustrates a block diagram of one embodiment of the controller 104. Generally, the controller 104 is comprised of one or more driver circuits 200 and receiver circuits 202. The driver circuits 200 are generally responsible for providing the stimulating signals over the lines 106 to the electrodes 108. That is, a processor 204, operating under software or hardware control, may instruct the driver circuit 200 to produce a stimulating signal having a set of preselected, desired parameters, such as frequency, duty cycle, duration, waveform shape, amplitude, voltage and magnitude. As noted above, driver circuits 200 may optionally include circuits 201 [not shown] to generate high-voltage defibrillation stimulation to the heart on leads 106 using subcutaneous or other NST electrodes 108.

The receiver circuits 202 are generally responsible for receiving signals from the optional one or more physiologic sensors, and processing those signals into a form, such as a digital format, which may be analyzed by the processor 204 and/or stored in a memory 206, such as a dynamic random access memory (DRAM). The memory 206 may also store software, which is used to control the operation of the processor 204. Cardiac signals can be filtered with a hardware filter or digitally, especially when the sensing of cardiac signals is interfered with by the local neurological stimulation therapy (as shown and described hereinbelow in relation to FIG. 8).

In one embodiment, signals stored in memory 206 may be transferred via a communication circuit 207 such as a telemetry circuit to an external device 209 such as a programmer. These signals may be stored in the external device, or transferred via a network 211 to a remote system 213 which may be a repository or some other remote database. Network 211 may be an intranet, Internet system such as the world-wide web, or any other type of communication link.

Figure 3:
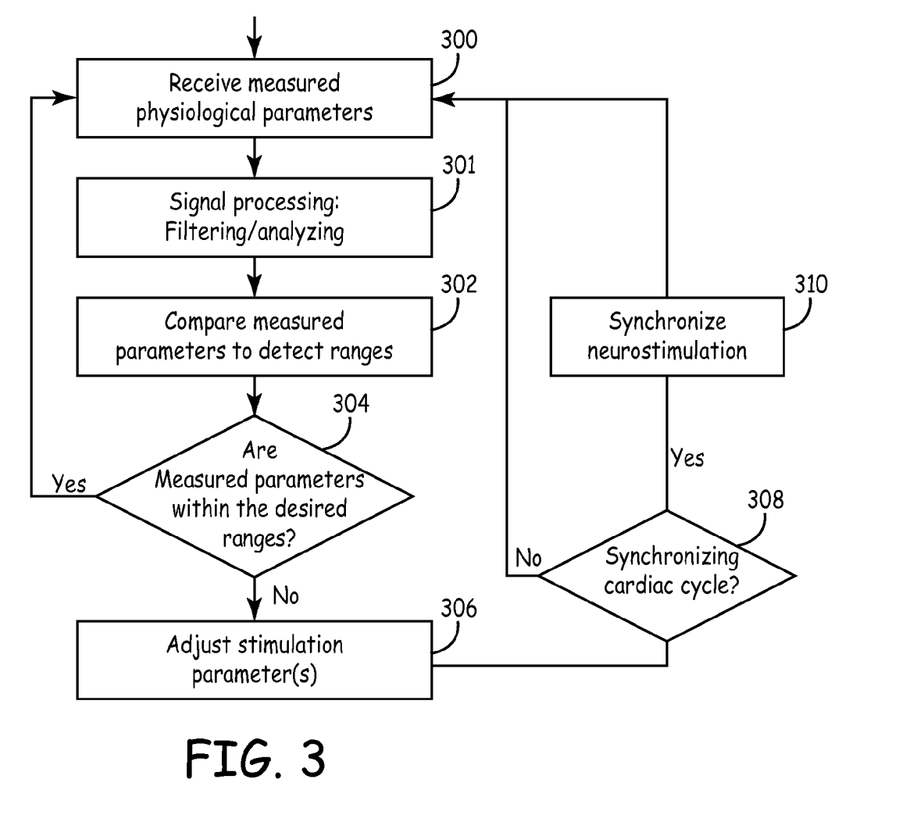
FIG. 3 illustrates a stylized flowchart of a control routine that may be performed by the controller of FIGS. 1 and 2.

The overall general operation of the controller 104 may be appreciated by reference to a flowchart depicted in FIG. 3. Those skilled in the art will appreciate that the flowchart illustrated herein may be used to represent either software that may be executed by the processor 204 or hardware configured to operate to perform the functions set forth in the flowchart. The process depicted in FIG. 3 begins at block 300 with the assumption that a cardiac event may have been detected either automatically or manually, but in any event, therapy is being administered by the controller 104.

At block 300, the processor 204 receives the measured physiological parameters via the receiver circuits 202. At block 301, signal processor occurs to improve the signal to noise ratio and remove spurious signals or the like. At block 302, the processor 204 compares the measured parameters to corresponding desired ranges. If the measure parameters are within the desired range, as determined at block 304, the processor 204 returns to block 300 and the process repeats. On the other hand, if the measured parameters fall outside the desired range, then the processor 204 at block 306 adjusts the stimulation parameter, which should result in the physiological parameters of the patient being adjusted to fall within the desired range. Then, in one form of the invention, at decision step 308 the neurostimulation therapy is optionally synchronized to the cardiac cycle. In the event that the decision is affirmative then the method proceeds to block 310 wherein the neurostimulation therapy is adjusted to occur (or not occur) during all or a part of the cardiac cycle. Thereafter, the process returns to block 300 and the process begins anew.

It should be appreciated that, owing to physiological differences between patients, an adjustment to the stimulation parameters may not produce an immediate, precise change in all patients. Rather, it is anticipated that each patient will respond substantially uniquely to variations in the stimulation parameters. Thus, it may be useful to add controllable variability to the operation of the feedback arrangement described herein. For example, it may be useful to control the rate at which the stimulation parameters are allowed to change, or to develop a histogram for a particular patient. The inventive system could include the ability to record parameters associated with the delivered NST such as pulse widths, frequencies, duty cycles, and time varying patterns. These parameters and the patient's response may be recorded in the memory 206, for example. Based on patient response, the efficacy of the NST can be evaluated so that the delivered NST can be adjusted to further improve cardiac performance and efficiency. This "learning" capability allows the system to optimize NST delivery based on prior patient data so that treatment is automatically tailored to individual patient needs. Furthermore, within a particular patient it may be useful for the device to tailor its therapy based on prior learning. For example, the onset or character of cardiac events may differ from episode to episode. It may be useful for the system to recognize multiple types of events (differing in, for example, severity, rate of onset, time of day or occurrence, patient activity levels, etc.) and treat these events with a uniquely tailored set of treatment parameters. Again, the device memory may be used to record parameters and patient responses to tailor treatments to different patterns of parameters.

In an alternative embodiment, a combined neuro and pacing stimulator Implantable Pulse Generator with outputs for neural stimulation (e.g. SCS, TENs, sub-cutaneous, peripheral, etc.) is provided. Lead attachments may be provided, in one instance, by a PISCES QUAD-type lead commercially-available from Medtronic Corporation, or an equivalent. Stimulation may be used in conjunction with cardiac resynchronization or other pacing therapy to improve cardiac function and may further be optimized based on some diagnostic parameter such as pressure, impedance, volume, or dimension, as discussed above. The Implantable Pulse Generator may further include a drug delivery system so that drug therapy to improve cardiac function may be automatically titrated with the stimulation. The implantable pulse generator may further includes a patient monitoring, diagnostic, or management system so that diagnostic and patient information therapy to improve cardiac function may be used in conjunction with neural stimulation.

In another embodiment, Spinal Cord Stimulation (SCS) may be performed at cervical levels C1-C8 instead of, or in addition to, T1-T12 stimulation. In yet another embodiment, Peripheral Nerve Stimulation (PNS) may be performed at C2, C3, median, peroneal, ulnar, ansa lenticularis, and/or dorsal root ganglia to improve cardiac performance and efficiency.

In many of the above-described embodiments, the electrical stimulation is described as SCS therapy, which may be delivered using one or more implanted electrodes located adjacent the spine, for example. However, it will be understood that stimulation using externally-applied electrodes, or subcutaneous electrodes located under the skin may also be used to obtain the benefits discussed above. In the case of an externally-applied electrode system, a portable stimulation device carried or worn externally by the patient may be used to provide treatment. Moreover, in a general form of the invention the neurological therapy comprises any electrical stimulation and the site for the therapy delivery also serves as the remote-sensing site for gathering cardiac activity signals.

In one embodiment, a paddle-type (flat) lead having a surface area between one square cm and five square inches or more may be used to accomplish the subcutaneous stimulation. Such a lead may be formed of an insulative material, with programmable electrodes on one or more of the flat sides of the lead for either skin stimulation, muscle stimulation, or both.

In one embodiment, electrodes may be provided on both sides of the lead, with the electrodes employed for stimulation at a given time being selectively enabled by a user. Alternatively, the system may be programmable to select the type of tissue to be stimulated. This is desirable since in some instances, it may be beneficial to provide stimulation to only spinal neurons, whereas in other instances it may be desirable to also stimulate skin nerves, muscle nerves, peripheral nerves, cranial nerves, such as the vagus, ganglia and plexi, or any combination of such nervous tissue. Various electrode combinations could be provided to allow for selectively enabling the stimulation in this manner.

In another embodiment, the paddle-type lead is between four and ten millimeters wide to easily pass through a twelve-gage needle before it unfolds. A special needle may be provided having an oval or rectangular cross-section of appropriate size to allow for the delivery of this type of lead. Electrodes may be provided on one or both sides of the paddle lead. In yet another embodiment, the electrodes of a cutaneous stimulation system could be placed on the chest wall, or a stimulation source may be attached to leads passed via needles to one or more subcutaneous sites. Alternatively, electrodes may be placed on an outside surface of an implanted pulse generator or pacing device or may be of the type integrally formed with the can, shell, or housing of an implantable device.

Figure 4:
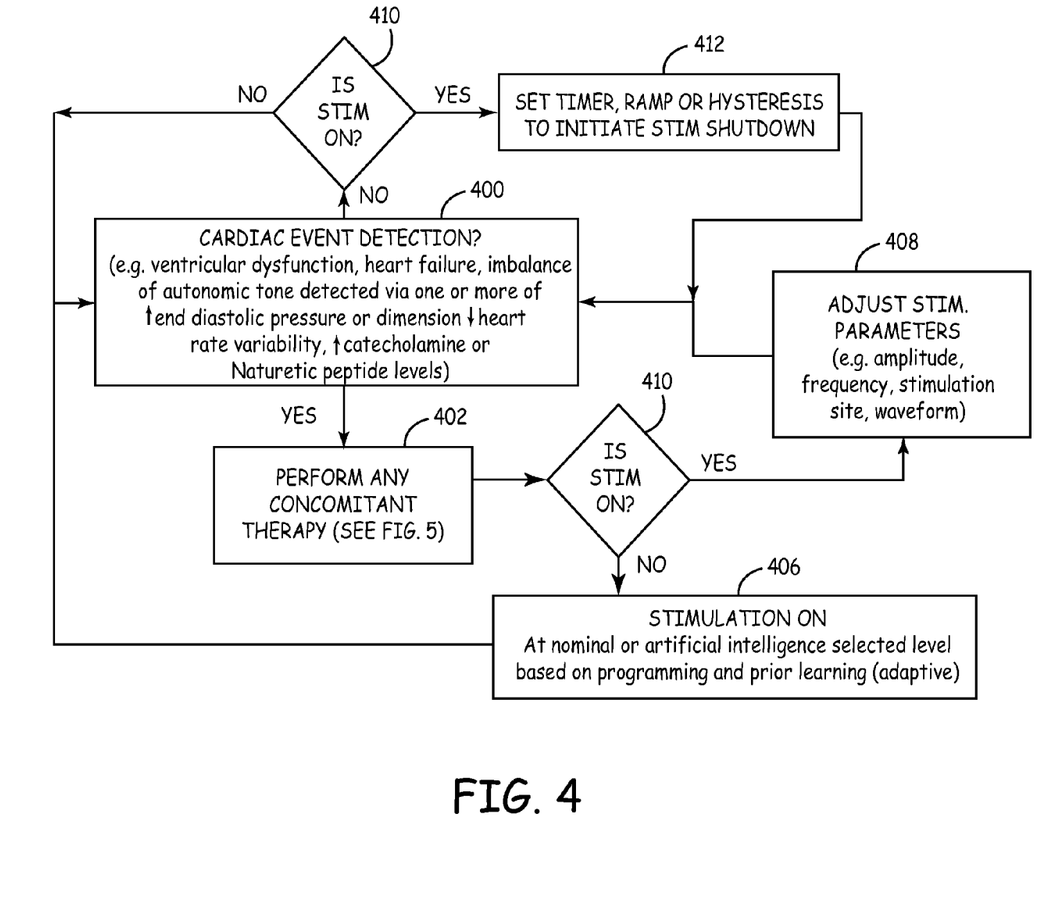
FIG. 4 is a flowchart illustrating one embodiment of the current invention.

FIG. 4 is a flowchart illustrating one embodiment of the current invention. A cardiac event such as ventricular dysfunction, heart failure, or imbalance of autonomic tone or neuro-endrocrinological system may be detected using measurable parameters such as increased diastolic pressure, a lower heart rate variability, increased catecholiamine levels, or a change in naturetic peptide levels (400). If a cardiac event is detected, any concomitant therapies are performed (402). If neural stimulation is not on (404), it is activated (406). This therapy delivery may involve use of artificial intelligence or other learning capability, as discussed above. Monitoring continues to determine whether the cardiac condition still exists (400). Returning to step 404, if neural stimulation is already on, stimulation parameters may be adjusted using physiological signals that may be sensed by one or more physiologic sensors, and monitoring continues with step 400.

In block 400, if a cardiac event has terminated, processing continues to step 410, where it is determined whether stimulation is on. If not, processing continues with monitoring step 400. Otherwise, stimulation deactivation is initiated (412). This may involve a hysteresis so that stimulation is terminated gradually over a predetermined period of time.

Figure 5:
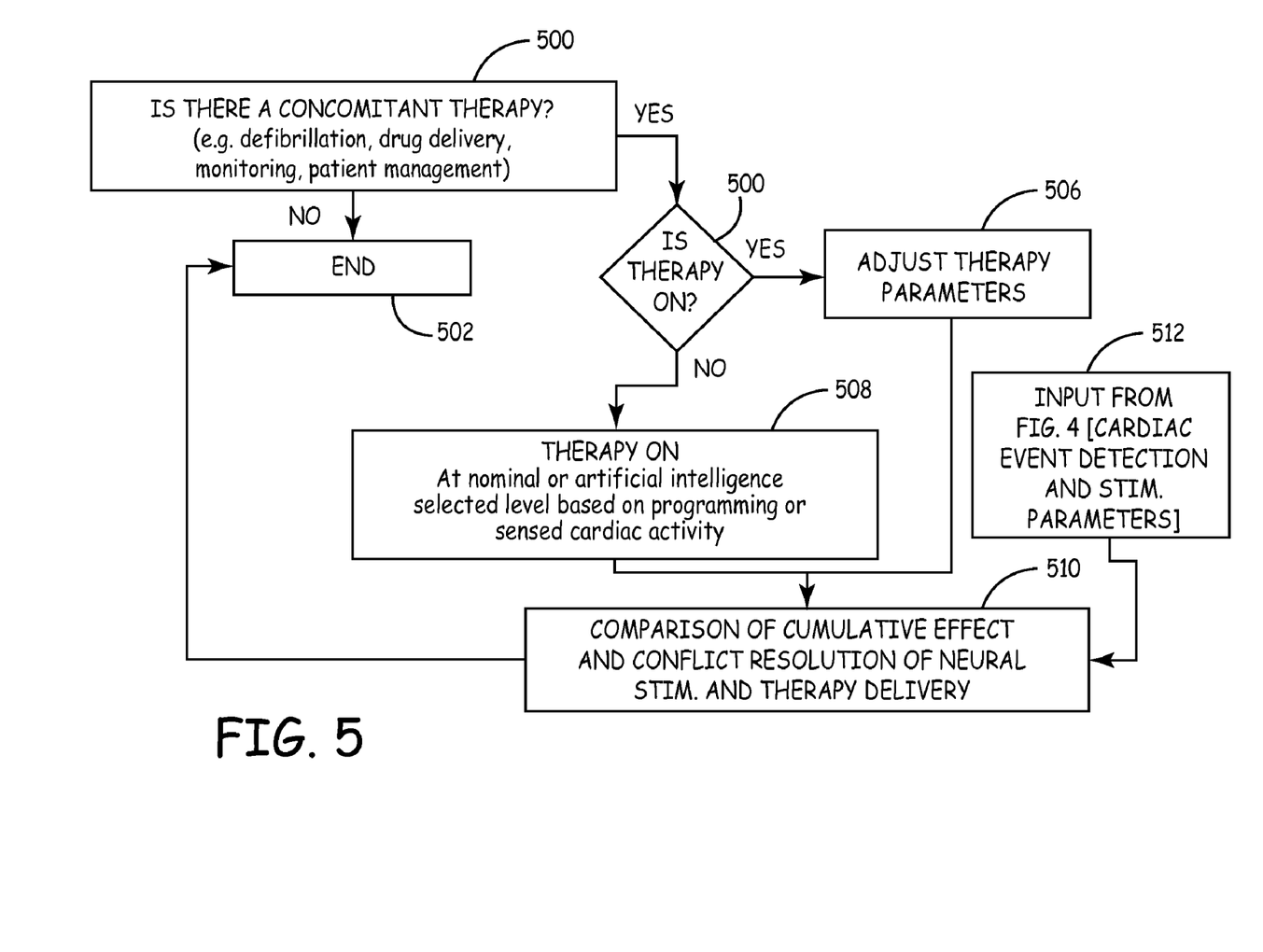
FIG. 5 is a flowchart illustrating one embodiment of concomitant therapy delivery that may be provided in conjunction with neural stimulation.

FIG. 5 is a flowchart illustrating one embodiment of concomitant therapy delivery that may be provided in conjunction with neural stimulation. This therapy corresponds to that shown in step 402 of FIG. 4. This type of therapy may involve pacing, defibrillation, drug delivery, monitoring, and/or patient management therapies, for example (500). If such a therapy is not enabled, no action is taken (502). Otherwise, if the therapy is on (504), therapy parameters may be adjusted (506). This may be performed using sensed physiological parameters, for example. If therapy is not enabled, this therapy is activated (508). Therapy delivery may be based on the results of previously-delivered therapy in the manner discussed above, as may be accomplished using artificial intelligence capabilities, for example. In either event, processing continues by comparing the cumulative effects of neural stimulation and the other therapy delivery so that the therapy delivery may be adjusted, if necessary (510). For example, delivery of stimulation to nerve tissue could increase pacing thresholds associated with a concomitant pacing therapy. As a result, the pacing therapy may need to be adjusted. In another example, delivery of stimulation according to the current invention may reduce pulse pressure, whereas a bi-ventricular pacing regimen increases the pulse pressure. It may be desirable to monitor this interaction and adjust one or more therapies as needed. This step is performed using information provided by the sensors, the neural stimulation system, and the concomitant therapy system(s), as shown in block 512.

Figure 6:
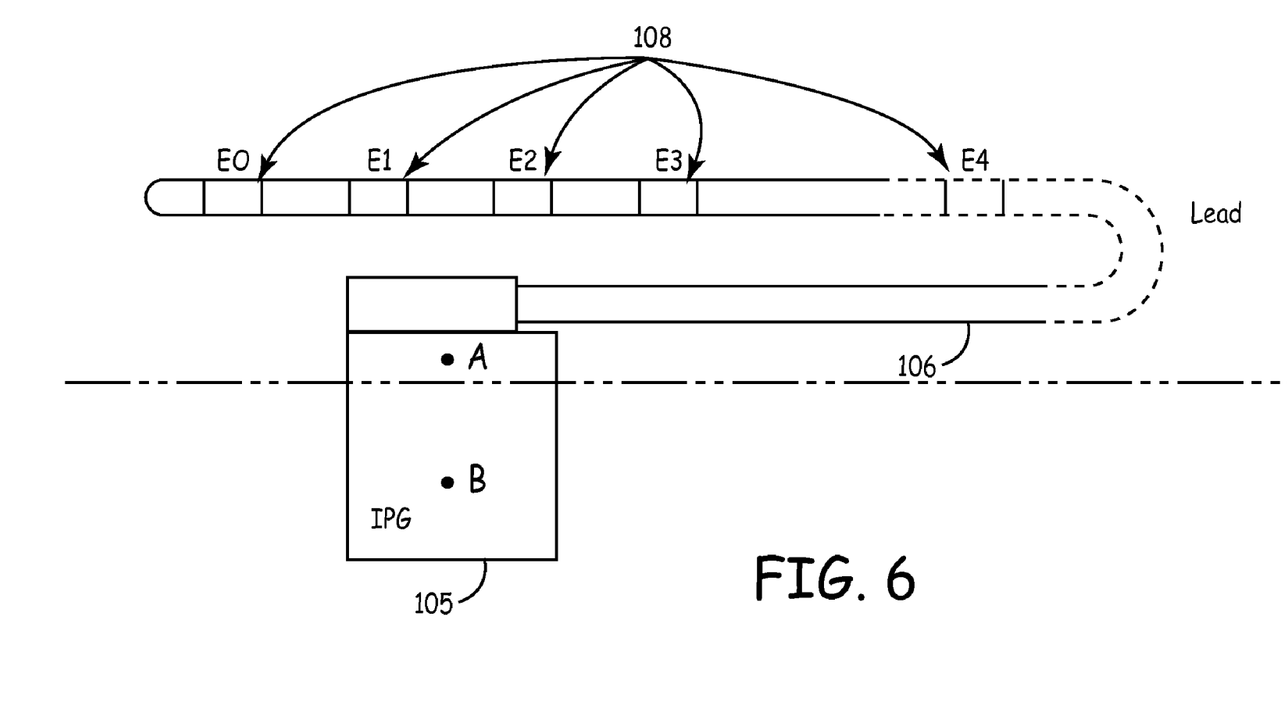
FIG. 6 is a schematic depiction of a neurological implantable pulse generator (IPG) coupled to a multi-electrode neurological medical electrical lead.

Referring now to FIG. 6, the following figure shows a schematic representation of a neurological stimulation lead 106 and a device body 105. Cardiac electrical signals can be sensed with (1) any combinations between electrodes 108 (labeled EO-E4 in FIG. 6) on a neurological lead 106 and/or on an surface portion (labeled A,B in FIG. 6) of a housing for device 105, or the conductive housing itself, and (2) with a hardware/digital filter(s) similar to or different from existing cardiac rhythm management (CRM) devices such as a pacemaker or implantable cardioverter-defibrillator (ICD), as is known in the art. Sensing electrodes 108 (EO-E4) are preferably located in an epidural space (e.g., T1 and T3) and in particular can be used to enhance the detection of posterior myocardial ischemia and infarction, while sensing electrodes (or vectors) between lead electrodes and a conductive portion (A,B) of the implanted device 105 are used to record cardiac electrical signals similar to standard ECG recordings. The invention can involve using a unmodified existing neurological stimulation lead 106 and/or implements dedicated cardiac sensing electrodes operatively coupled to an existing neurological lead 106 and device 105. The configuration and number of electrodes utilized can vary, for example, a pair of neurological electrical leads each having eight discrete, addressable electrodes can be used. Algorithms for ischemia detection and other diagnostic features can be used to filter signal artifacts generated by a device or by myopotentials and the like. Additional filtering can also be applied.

In addition, the SCS electrodes 108 may be implanted proximate, on, adjacent or within a portion of a spinal cord.

Alternatively the SCS electrodes may be subcutaneously placed near the spinal cord, or cutaneously placed over a patient's skin near the spine. The SCS electrodes may be electrically connected to a controller or other components in the system through conductive leads or wires. The SCS electrodes may also be capable of bi-directional wireless communication with a controller or other components in the system.

Also, a variety of optional electrodes may be included in the system. Optional electrodes may be implanted, subcutaneously placed, or externally located. Optional electrodes may be adapted for performing a variety of functions, and may be placed at any location suitable for performing their intended functions. Optional electrodes may comprise, for example, nerve stimulation electrodes mounted on vagus or other nerves, muscle stimulation electrodes (spaced from any myocardial tissue), electrodes on transcutaneous electrical nerve stimulation units, etc. Optional electrodes may be electrically connected to controller or other components in the system through conductive leads or wires. Optional electrodes may also be capable of bi-directional wireless communication with controller or other components in the system. The primary and/or optional electrodes can be used to deliver a high voltage defibrillation therapy provided a potentially lethal arrhythmia can be discriminated from, for example, a sinus tachycardia or the like.

For example, in one embodiment a single SCS electrode is located on a distal portion of an SCS lead, more than four SCS electrodes can be arranged in a linear fashion, or six SCS electrodes can be arranged in a pattern (e.g., diamond, rectangle, etc.). In one form of the invention up to eight SCS electrodes are arranged in two substantially parallel lines. The SCS electrode configurations are examples used for illustration purposes only and are not meant to be limiting A controller can operatively coupled within a housing disposed in a fully-implanted location, subcutaneously placed or externally located. The controller can of course be constructed of a conductive housing. Optionally, any number of electrodes adapted to sense cardiac electrical signals may be exposed on a portion of an outer surface of the housing and electrically insulated from the housing. The electrodes can be iteratively tested so that the pair or plurality that produces the best sensing results can be programmed for chronic use.

The processor controls the time periods during which sensing of cardiac electrical signals may be performed. For example, the processor can be programmed to sense cardiac activity only when SCS therapy is not being delivered by any of the SCS electrodes. Alternatively, the processor may suspend all spinal cord stimulation to initiate sensing, and then resume SCS or other NST therapy after cardiac sensing and/or detection is completed. Alternatively, the processor can sense the QRS complex of cardiac activity signals and deliver a pulse train (e.g., 100-200 ms) of neurological stimulation during the refractory period so to avoid the interference of cardiac sensing artifacts from neurological stimulation. The processor can coordinate sensing functions with the functions of any optional electrodes, physiologic sensors or any other optional medical devices.

Figure 7:
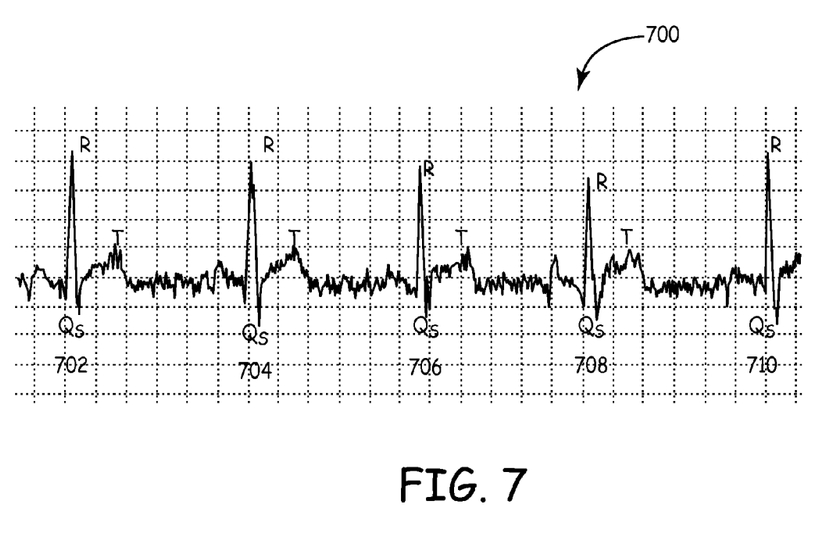
FIG. 7 is a temporal trace of cardiac activity signals collected using SCS electrodes spaced from a canine heart and clearly depicts the deflections of the cardiac cycle.
Figure 8:
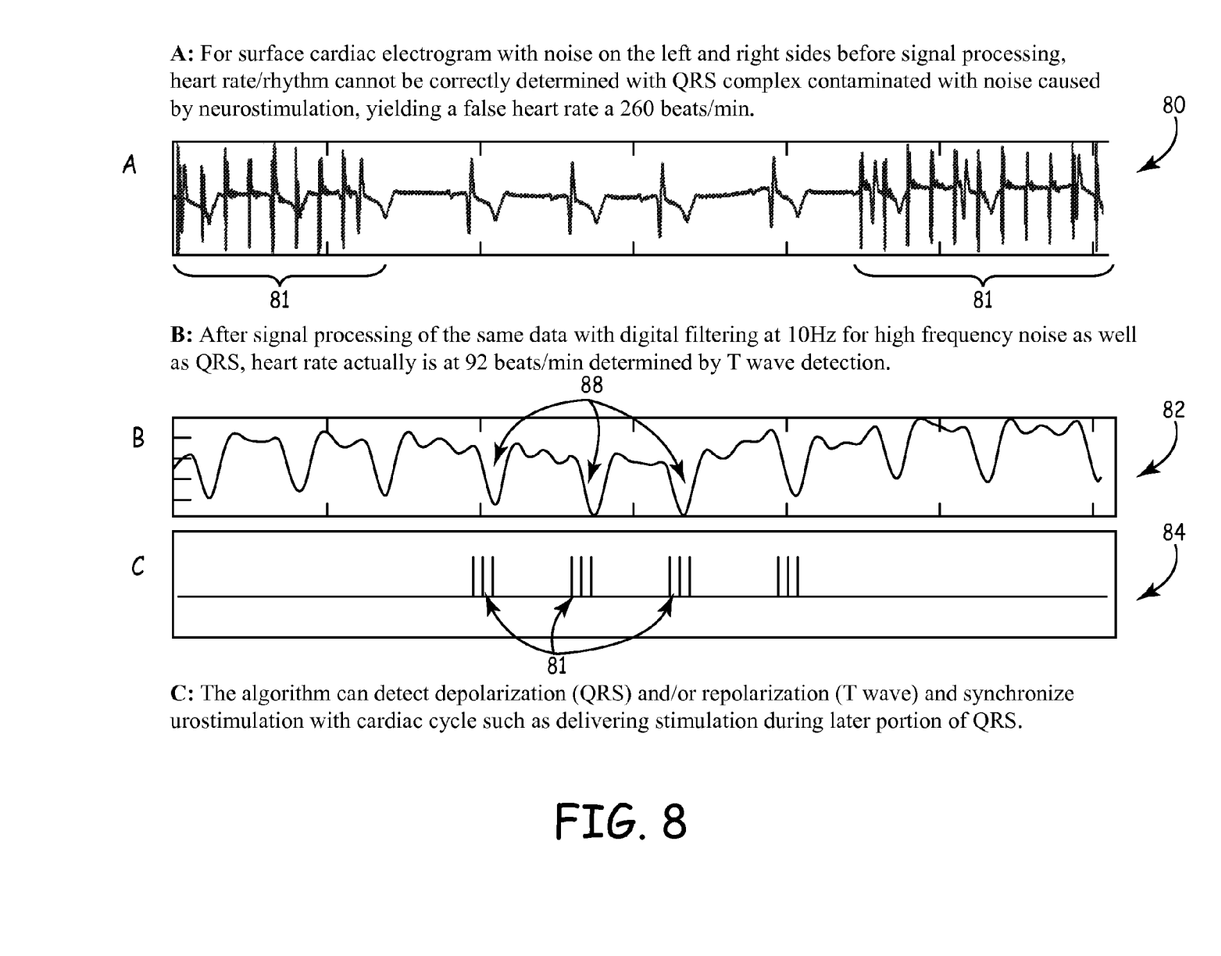
FIGS. 8A-C depict three temporal tracings of signals wherein drawing A depicts essentially raw, unfiltered data (e.g., localized neural stimulation pulses and remote-field cardiac activity signals), drawing B depicts a filtered version of the data depicted in drawing A, and drawing C depicts neurological stimulation being delivered with a predetermined portion of the cardiac activity (i.e., during myocardial repolarization, or T-wave, events).

FIG. 7 is a temporal trace of cardiac activity signals 700 collected using SCS electrodes spaced from a canine heart and clearly depicting the well-known QRS-T deflections of the ventricular depolarization-repolarization sequences (denoted by their respective letter in FIG. 7) of a plurality of cardiac cycles 702,704,706,708,710.

FIGS. 8A-C depict three temporal tracings of signals wherein drawing A depicts essentially raw, unfiltered data 80 (e.g., localized neural stimulation pulses 81 and remote-field cardiac activity signals), drawing B depicts a filtered version 82 of the data depicted in drawing A (81), and drawing C depicts pulawa od neurological stimulation 86 being delivered with a predetermined portion of the cardiac activity (i.e., during myocardial repolarization, or T-wave, events 88). These drawings provide just one aspect of the notion of linking neurological stimulation to certain parts or phases of cardiac activity and are in addition to the basic premise of the invention; namely, remote monitoring of cardiac activity using neurological electrodes spaced apart from the heart (e.g., disposed in electrical communication with a portion of the vagus nerve above the cardiac branch). In one form of the invention the neurological therapy delivery is intended to benefit the cardiovascular system of a patient, in other forms any impact on the system might be deemed indirect (e.g., providing neurological stimulation to treat epilepsy, obesity, depression, or the like).

From the foregoing discussion, one skilled in the art will appreciate that the current system and method for treating ventricular dysfunction, heart failure, or imbalance of the autonomic tone allows the treatment to be titrated using a single dorsally-located SCS system or other NST system. The particular embodiments disclosed and depicted herein are intended as illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

The invention claimed is:

1. A method for monitoring cardiac activity, comprising the steps of:
   placing a plurality of electrodes adapted to serve as a source of electrical neurological stimulation adjacent to, on or within a portion of spinal tissue of a patient;
   sensing cardiac ECG signals using said plurality of electrodes, wherein each of said plurality of electrodes is spaced from myocardial tissue of the patient; and
   delivering a neurological therapy to the spinal tissue via said plurality of electrodes in response to the sensed ECG signals; and further comprising:
   detecting a cardiac event from the ECG signals;
   recognizing a characteristic of an onset of the cardiac event;
   delivering the neurological therapy in response to the cardiac event;
   recording a patient response to the neurological therapy; and
   tailoring a set of neurological therapy treatment parameters in response to the recorded patient response and the recognized onset characteristic.

2. The method of claim 1 wherein the onset characteristic includes one of a time of day, a rate of onset, and a patient activity level.

3. A method for monitoring cardiac activity, comprising the steps of:
   placing a plurality of electrodes adapted to serve as a source of electrical neurological stimulation adjacent to, on or within a portion of spinal tissue of a patient;
   sensing cardiac ECG signals using said plurality of electrodes, wherein each of said plurality of electrodes is spaced from myocardial tissue of the patient; and delivering a neurological therapy to the spinal tissue via said plurality of electrodes in response to the sensed ECG signals,
wherein sensing the ECG signals comprises sensing QRS deflections, wherein delivering the neurological therapy comprises delivering a pulse train of neurological stimulation during a refractory period of the sensed cardiac QRS deflections.

* * * * *